(12) United States Patent
Molinier et al.

(10) Patent No.: US 11,377,399 B2
(45) Date of Patent: Jul. 5, 2022

(54) XYLENE PRODUCTION PROCESSES AND SYSTEMS

(71) Applicant: ExxonMobil Chemical Patents Inc., Baytown, TX (US)

(72) Inventors: Michel Molinier, Houston, TX (US); Hari Nair, Spring, TX (US); Scott J. Weigel, Allentown, PA (US); Michael Salciccioli, Ann Arbor, MI (US); Doron Levin, Highland Park, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 41 days.

(21) Appl. No.: 16/759,866

(22) PCT Filed: Nov. 15, 2018

(86) PCT No.: PCT/US2018/061295
§ 371 (c)(1),
(2) Date: Apr. 28, 2020

(87) PCT Pub. No.: WO2019/112769
PCT Pub. Date: Jun. 13, 2019

(65) Prior Publication Data
US 2021/0032182 A1  Feb. 4, 2021

Related U.S. Application Data

(60) Provisional application No. 62/594,630, filed on Dec. 5, 2017.

(51) Int. Cl.
*C07C 2/64* (2006.01)
*C07C 4/18* (2006.01)
(Continued)

(52) U.S. Cl.
CPC ............. *C07C 2/64* (2013.01); *B01J 19/0046* (2013.01); *C07C 4/08* (2013.01); *C07C 4/12* (2013.01);
(Continued)

(58) Field of Classification Search
CPC .. C07C 2/64; C07C 2/864; C07C 4/08; C07C 4/12; C07C 4/18; C07C 6/123;
(Continued)

(56) References Cited

U.S. PATENT DOCUMENTS 3,478,120 A * 11/1969 Myers ...................... C07C 4/12
585/489
3,919,339 A   11/1975 Ransley
(Continued)

OTHER PUBLICATIONS

J. Crank, The Mathematics of Diffusion, Oxford University Press, Ely House, London, 1967.

*Primary Examiner* — Youngsul Jeong
*Assistant Examiner* — Jason Y Chong

(57) ABSTRACT

A process and related system for producing para-xylene (PX). In an embodiment, the process includes (a) separating a feed stream comprising $C_{6+}$ aromatic hydrocarbons into a toluene containing stream and a $C_{8+}$ hydrocarbon containing stream and (b) contacting at least part of the toluene containing stream with a methylating agent in a methylation unit to convert toluene to xylenes and produce a methylated effluent stream. In addition, the process includes (c) recovering PX from the methylated effluent stream in (b) to produce a PX depleted stream and (d) transalkylating the PX depleted stream to produce a transalkylation effluent stream. The transalkylation effluent stream includes a higher concentration of toluene than the PX depleted stream. Further, the process includes (e) converting at least some ethylbenzene (EB) within the $C_{8+}$ hydrocarbon containing stream (Continued)

into toluene and (f) flowing the toluene converted in (e) to the contacting in (b).

20 Claims, 3 Drawing Sheets

(51) Int. Cl.
    *C07C 15/08*     (2006.01)
    *C07C 4/08*     (2006.01)
    *C07C 4/12*     (2006.01)
    *B01J 19/00*     (2006.01)
    *C07C 6/12*     (2006.01)
    *C07C 7/00*     (2006.01)

(52) U.S. Cl.
    CPC ................ *C07C 4/18* (2013.01); *C07C 6/123* (2013.01); *C07C 7/005* (2013.01); *B01J 2219/00006* (2013.01); *C07C 15/08* (2013.01)

(58) Field of Classification Search
    CPC ........... C07C 7/005; C07C 7/13; C07C 15/08; C07C 5/2729; B01J 19/0046; B01J 2219/00006; B01J 37/0009; B01J 37/10; B01J 35/0006; B01J 29/40; B01J 29/48; B01J 29/7469; B01J 29/80; Y02P 20/52; C10G 2300/104; C10G 2400/30; C10G 29/205; C10G 35/00; C10G 35/095; C10G 45/68; C10G 50/00; C10G 59/00; C10G 69/00
See application file for complete search history.

(56) References Cited

U.S. PATENT DOCUMENTS

| | | |
|---|---|---|
| 4,016,218 A | 4/1977 | Haag et al. |
| 4,177,219 A | 12/1979 | Bertolacini et al. |
| 4,356,338 A | 10/1982 | Young |
| 5,110,776 A | 5/1992 | Chitnis et al. |
| 5,231,064 A | 7/1993 | Absil et al. |
| 5,348,643 A | 9/1994 | Absil et al. |
| 5,563,310 A | 10/1996 | Chang et al. |
| 6,423,879 B1 | 7/2002 | Brown et al. |
| 6,504,072 B1 | 1/2003 | Brown et al. |
| 6,642,426 B1 | 11/2003 | Johnson et al. |
| 8,168,845 B2 | 5/2012 | Porter et al. |
| 8,481,798 B2 | 7/2013 | Schaefer et al. |
| 8,529,757 B2 | 9/2013 | Go et al. |
| 8,569,564 B2 | 10/2013 | Porter et al. |
| 8,580,120 B2 | 11/2013 | Porter et al. |
| 9,522,863 B2 | 12/2016 | Bender et al. |
| 2005/0010074 A1* | 1/2005 | Iwayama ................ B01J 29/40 585/481 |
| 2014/0100402 A1 | 4/2014 | Gawlik et al. |
| 2015/0376086 A1 | 12/2015 | Tinger et al. |
| 2015/0376088 A1* | 12/2015 | Molinier ................ C07C 6/123 585/314 |
| 2016/0220987 A1 | 8/2016 | Lai et al. |
| 2016/0221895 A1 | 8/2016 | Lai et al. |
| 2016/0221896 A1 | 8/2016 | Elia et al. |

\* cited by examiner

XYLENE PRODUCTION PROCESSES AND SYSTEMS

CROSS-REFERENCE OF RELATED APPLICATIONS

This application is a U.S. national phase application of PCT application No. PCT/US2018/061295 having a filing date of Nov. 15, 2018, which claims priority to and the benefit of U.S. provisional application Ser. No. 62/594,630 having a filing date of Dec. 5, 2017, the contents of both of which are incorporated by reference in their entirety.

TECHNICAL FIELD

This disclosure generally relates to processes and systems for the production of xylenes and more particularly for the production of para-xylene (PX).

BACKGROUND

A major source of xylenes is catalytic reformate, which is produced by contacting petroleum naphtha with a hydrogenation/dehydrogenation catalyst on a support. The resulting reformate is a complex mixture of paraffins and $C_6$ to $C_8$ aromatics, in addition to a significant quantity of heavier aromatic hydrocarbons. After removing the light ($C_{5-}$) paraffinic components, the remainder of reformate is normally separated into $C_{7-}$, $C_8$, and $C_{9+}$ containing fractions using a plurality of distillation steps. Benzene can then be recovered from the $C_{7-}$ containing fraction to leave a toluene-rich fraction which is generally used to produce additional $C_8$ aromatics by toluene disproportionation and/or transalkylation with part of the $C_{9+}$ aromatics containing fraction. The $C_8$ containing fraction is fed to a xylene production loop where PX is recovered, generally by adsorption or crystallization, and the resultant PX depleted stream is subjected to catalytic conversion to isomerize the xylenes back towards equilibrium distribution. The resultant isomerized xylene stream (which may include all of the xylene isomers at their equilibrium concentrations) can then be recycled to the PX recovery unit.

Although benzene and toluene are important aromatic hydrocarbons, the demand for xylenes, particularly PX, outstrips that for benzene and toluene and currently is growing at an annual rate of 5-7%. There is therefore a continuing need to develop aromatics production technologies which maximize the production of PX, while minimizing the associated capital and operating costs.

BRIEF SUMMARY

Embodiments disclosed herein are directed to systems, and processes that allow for the recovery of PX from an effluent stream produced from a methylation unit. In at least some embodiments, a PX depleted stream is flowed to a transalkylation unit to increase the amount of toluene in the PX depleted stream and/or to convert heavier (e.g., $C_9$-$C_{11}$) aromatics to xylenes. At least some of the resulting effluent from the transalkylation unit may then be recycled to the methylation unit for further subsequent recovery of PX. In at least some embodiments, no isomerization units are included, so that the capital and operating expenses for such units may be avoided, and the overall costs required for the production of PX may be decreased. In addition, in at least some embodiments disclosed herein, ethylbenzene (EB) within the catalytic reformate is converted into additional toluene that is then used to supplement the feed to the methylation unit and therefore further increase the recovery of PX.

Some particular embodiments disclosed herein are directed to processes for recovering PX. In an embodiment, the process includes (a) separating a feed stream comprising $C_{6+}$ aromatic hydrocarbons into at least a toluene containing stream and a $C_{8+}$ hydrocarbon containing stream and (b) contacting at least part of the toluene containing stream with a methylating agent in a methylation unit under conditions effective to convert toluene to xylenes and produce a methylated effluent stream. In addition, the process includes (c) recovering PX from the methylated effluent stream in (b) to produce a PX depleted stream and (d) transalkylating the PX depleted stream to produce a transalkylation effluent stream. The transalkylation effluent stream includes a higher concentration of toluene than the PX depleted stream. Further, the process includes (e) converting at least some ethylbenzene (EB) within the $C_{8+}$ hydrocarbon containing stream into toluene and (f) flowing the toluene converted in (e) to the contacting in (b).

Other particular embodiments disclosed herein are directed to systems for recovering PX. In an embodiment, the system includes a catalytic reformer configured to produce a reformate stream comprising $C_{6+}$ aromatic hydrocarbons from a naphtha feedstock and a first separation system downstream of the catalytic reformer. The first separation system is configured to separate the reformate stream into at least a toluene containing stream and a $C_{8+}$ hydrocarbon containing stream. In addition, the system includes a de-methylation unit configured to receive the $C_{8+}$ hydrocarbon containing stream and convert at least some ethylbenzene (EB) within the $C_{8+}$ hydrocarbon containing stream into toluene. Further, the system includes a toluene methylation unit downstream of the first separation system and the de-methylation unit. The toluene methylation unit is configured to receive the toluene containing stream and toluene converted from EB in the de-methylation unit, and to react toluene with a methylating agent to produce xylenes that are emitted from the toluene methylation unit as a methylated effluent stream. Still further, the system includes a second separation system downstream of the toluene methylation unit. The second separation system is configured to recover PX from the methylated effluent stream and produce a PX depleted stream. Also, the system includes a transalkylation unit downstream of the second separation system. The transalkylation unit is configured to transalkylate the PX depleted stream and produce a transalkylation effluent stream that has a higher concentration of toluene than the PX depleted stream.

DETAILED DESCRIPTION

Figure 1:
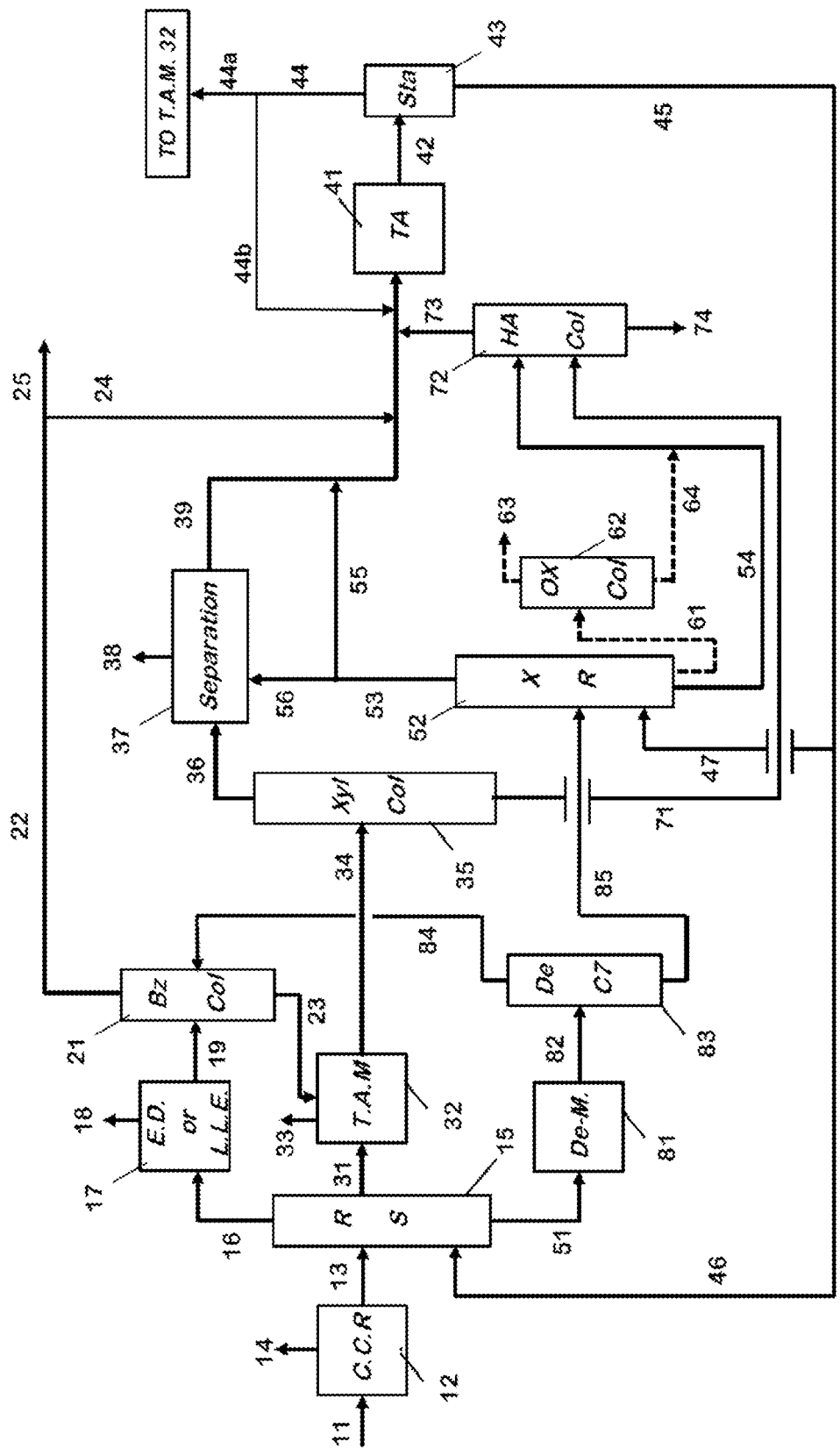
FIG. 1 is a flow diagram of a process and system for producing PX from catalytic reformate according to at least some embodiments disclosed herein.

The following discussion is directed to various embodiments. However, it should be appreciated that the embodiments disclosed herein have broad application, and that the discussion of any embodiment is meant only to be exemplary of that embodiment, and not intended to suggest that the scope of the disclosure, including the claims, is limited to that embodiment. In the drawings, certain features and components herein may be shown exaggerated in scale or in somewhat schematic form and some details of conventional elements may not be shown in interest of clarity and conciseness. All documents described herein are incorporated by reference, including any priority documents and/or testing procedures, to the extent they are not inconsistent with this text. When numerical lower limits and numerical upper limits are listed herein, ranges from any lower limit to any upper limit are contemplated.

As used herein, the term "$C_n$" hydrocarbon wherein n is a positive integer, e.g., 1, 2, 3, 4, or 5, means a hydrocarbon having n number of carbon atom(s) per molecule. In addition, as used herein the term "$C_{n+}$" hydrocarbon wherein n is a positive integer, e.g., 1, 2, 3, 4, or 5, means hydrocarbon having at least n number of carbon atom(s) per molecule. Further, the term "$C_{n-}$" hydrocarbon wherein n is a positive integer, e.g., 1, 2, 3, 4, or 5, means a hydrocarbon having no more than n number of carbon atom(s) per molecule. As used herein the term "aromatics" means hydrocarbon molecules containing at least one aromatic core. As used herein the term "hydrocarbon" encompasses mixtures of hydrocarbon, including those having different values of n. As used herein and unless otherwise specified, the terms "approximately," "substantially," "about," mean+/−10%.

As previously described, there is a continuing need to develop aromatics production technologies that maximize PX production, while minimizing the associated capital and operational costs thereof. Accordingly, embodiments disclosed herein include systems and processes for recovering PX from an effluent stream produced from a methylation unit being fed a $C_7$ hydrocarbon stream from catalytic reformate. In at least some embodiments, a PX depleted stream resulting from the recovery of PX is routed to a transalkylation unit to increase an amount of toluene in the PX depleted stream and/or to convert heavier (e.g., $C_9$-$C_{11}$) aromatics to xylenes. Thereafter, at least some of the toluene emitted from the transalkylation unit is recycled to the methylation unit. As a result, in at least some embodiments, the PX depleted stream is not flowed through a xylenes isomerization unit, so that the capital and operating expenses of such units may be avoided. Additionally, EB disposed within the catalytic reformate is converted into additional toluene that is further supplied to the methylation unit, thereby further increasing the yield of PX.

Any method known in the art for adding methyl groups to a phenyl ring can be used in the methylation step of the embodiments disclosed herein. However, in certain embodiments, the methylation step employs a highly para-selective methylation catalyst, such as that employed in U.S. Pat. Nos. 6,423,879 and 6,504,072, the entire contents of which are incorporated herein by reference. Such a catalyst comprises a molecular sieve having a Diffusion Parameter for 2,2-dimethylbutane of about 0.1-15 sec$^{-1}$, such as 0.5-10 sec$^{-1}$, when measured at a temperature of 120° C. and a 2,2-dimethylbutane pressure of 60 torr (8 kPa). As used herein, the Diffusion Parameter of a particular porous crystalline material is defined as $D/r^2 \times 10^6$, wherein D is the diffusion coefficient (cm$^2$/sec) and r is the crystal radius (cm). The required diffusion parameters can be derived from sorption measurements provided the assumption is made that the plane sheet model describes the diffusion process. Thus, for a given sorbate loading Q, the value $Q/Q_\infty$, where $Q_\infty$ is the equilibrium sorbate loading, is mathematically related to $(Dt/r^2)^{1/2}$ where t is the time (sec) required to reach the sorbate loading Q. Graphical solutions for the plane sheet model are given by J. Crank in "The Mathematics of Diffusion," Oxford University Press, Ely House, London, 1967, the entire contents of which are incorporated herein by reference.

The molecular sieve employed in the para-selective methylation process disclosed herein is normally a medium-pore size aluminosilicate zeolite. Medium pore zeolites are generally defined as those having a pore size of about 5 to about 7 Angstroms, such that the zeolite freely sorbs molecules such as n-hexane, 3-methylpentane, benzene, and PX. Another common definition for medium pore zeolites involves the Constraint Index test which is described in U.S. Pat. No. 4,016,218, which is incorporated herein by reference. In this case, medium pore zeolites have a Constraint Index of about 1-12, as measured on the zeolite alone without the introduction of oxide modifiers and prior to any steaming to adjust the diffusivity of the catalyst. Particular examples of suitable medium pore zeolites include ZSM-5, ZSM-11, ZSM-12, ZSM-22, ZSM-23, ZSM-35, ZSM-48, and MCM-22, with ZSM-5 and ZSM-11 being preferred in at least some embodiments.

The medium pore zeolites described above are particularly effective for the present methylation process since the size and shape of their pores favor the production of PX over the other xylene isomers (i.e., meta-xylene (MX), ortho-xylene (OX)). Conventional forms of these zeolites have Diffusion Parameter values in excess of the 0.1-15 sec$^{+1}$ range referred to above. However, the required diffusivity for the catalyst can be achieved by severely steaming the catalyst so as to effect a controlled reduction in the micropore volume of the catalyst to not less than 50%, and preferably 50-90%, of that of the unsteamed catalyst. Reduction in micropore volume is derived by measuring the n-hexane adsorption capacity of the catalyst, before and after steaming, at 90° C. and 75 torr n-hexane pressure.

Steaming of the zeolite is effected at a temperature of at least about 950° C., preferably about 950 to about 1075° C., and most preferably about 1000 to about 1050° C. for about 10 minutes to about 10 hours, preferably from 30 minutes to 5 hours.

To effect the desired controlled reduction in diffusivity and micropore volume, it may be desirable to combine the zeolite, prior to steaming, with at least one oxide modifier, such as at least one oxide selected from elements of Groups 2 to 4 and 13 to 16 of the Periodic Table. Most preferably, said at least one oxide modifier is selected from oxides of boron, magnesium, calcium, lanthanum, and most preferably phosphorus. In some cases, the zeolite may be combined with more than one oxide modifier, for example a combination of phosphorus with calcium and/or magnesium, since in this way it may be possible to reduce the steaming severity needed to achieve a target diffusivity value. In some embodiments, the total amount of oxide modifier present in the catalyst, as measured on an elemental basis, may be between about 0.05 and about 20 wt %, and preferably is between about 0.1 and about 10 wt %, based on the weight of the final catalyst.

Where the modifier includes phosphorus, incorporation of modifier into the catalyst is conveniently achieved by the methods described in U.S. Pat. Nos. 4,356,338, 5,110,776, 5,231,064 and 5,348,643, the entire disclosures of which are incorporated herein by reference. Treatment with phosphorus-containing compounds can readily be accomplished by contacting the zeolite, either alone or in combination with a binder or matrix material, with a solution of an appropriate phosphorus compound, followed by drying and calcining to convert the phosphorus to its oxide form. Contact with the phosphorus-containing compound is generally conducted at a temperature of about 25° C. and about 125° C. for a time between about 15 minutes and about 20 hours. The concentration of the phosphorus in the contact mixture may be between about 0.01 and about 30 wt %. Suitable phosphorus compounds include, but are not limited to, phosphonic, phosphinous, phosphorous and phosphoric acids, salts and esters of such acids and phosphorous halides.

After contacting with the phosphorus-containing compound, the porous crystalline material may be dried and calcined to convert the phosphorus to an oxide form. Calcination can be carried out in an inert atmosphere or in the presence of oxygen, for example, in air at a temperature of about 150 to 750° C., preferably about 300 to 500° C., for at least 1 hour, preferably 3-5 hours. Similar known techniques can be used to incorporate other modifying oxides into the catalyst employed in the alkylation process.

In addition to the zeolite and modifying oxide, the catalyst employed in the methylation process may include one or more binder or matrix materials resistant to the temperatures and other conditions employed in the process. Such materials include active and inactive materials such as clays, silica and/or metal oxides such as alumina. The latter may be either naturally occurring or in the form of gelatinous precipitates or gels including mixtures of silica and metal oxides. Use of a material which is active, tends to change the conversion and/or selectivity of the catalyst and hence is generally not preferred. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the porous crystalline material include the montmorillonite and kaolin family, which families include the subbentonites, and the kaolins commonly known as Dixie, McNamee, Ga. and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the porous crystalline material can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of porous crystalline material and inorganic oxide matrix vary widely, with the content of the former ranging from about 1 to about 90% by weight and more usually, particularly when the composite is prepared in the form of beads, in the range of about 2 to about 80 wt % of the composite. Preferably, the matrix material comprises silica or a kaolin clay.

The methylation catalyst used in the present process may optionally be precoked. The precoking step may be carried out by initially loading uncoked catalyst into the methylation reactor. Then, as the reaction proceeds, coke is deposited on the catalyst surface and thereafter may be controlled within a desired range, typically from about 1 to about 20 wt % and preferably from about 1 to about 5 wt %, by periodic regeneration through exposure to an oxygen-containing atmosphere at an elevated temperature.

Methylation of toluene in accordance with the present process can be effected with any known methylating agent, but preferred methylating agents include methanol and/or a mixture of carbon monoxide and hydrogen and/or dimethyl ether. It should be appreciated that in some embodiments, the aromatic component fed to the methylation unit includes at least some benzene in addition to or in lieu of toluene.

Suitable conditions for the methylation reaction include a temperature from 350 to 700° C., such as from 500 to 600° C., a pressure of from 100 and 7000 kPa absolute, a weight hourly space velocity of from 0.5 to 1000 hr−1, and a molar ratio of toluene to methanol (in the reactor charge) of at least about 0.2, e.g., from about 0.2 to about 20. The process may suitably be carried out in fixed, moving, or fluid catalyst beds. If it is desired to continuously control the extent of coke loading, moving or fluid bed configurations are preferred. With moving or fluid bed configurations, the extent of coke loading can be controlled by varying the severity and/or the frequency of continuous oxidative regeneration in a catalyst regenerator. One example of a suitable fluidized bed process for methylating toluene includes staged injection of the methylating agent at one or more locations downstream of the toluene feed location. Such a process in described in U.S. Pat. No. 6,642,426, the entire contents of which are incorporated herein by reference.

Using the processes of at least some of the embodiments disclosed herein, toluene can be alkylated with methanol so as to produce PX at a selectivity of at least about 75 wt % (based on total $C_8$ aromatic product) at a per-pass aromatic conversion of at least about 15 wt % and a trimethylbenzene production level less than 1 wt %. Unreacted toluene (and/or benzene) and methylating agent and a portion of the water by-product may be recycled to the methylation reactor and heavy byproducts routed to fuels dispositions. Similarly, as previously noted above, benzene can be alkylated with methanol so as to produce mostly toluene and byproduct PX at a selectivity of at least about 50 wt % (based on total $C_8$ aromatic product) at a per-pass aromatic conversion of at least about 15 wt % and a trimethylbenzene production level less than 1 wt %. Toluene product, unreacted benzene and methylating agent and a portion of the water by-product may be recycled to the methylation reactor and heavy byproducts routed to fuels dispositions. The $C_8$ fraction is routed to a PX separation section, which typically operates by fractional crystallization, selective adsorption, or both to recover a PX product stream from the alkylation effluent and leave a PX-depleted stream containing mainly $C_7$ and $C_8$ hydrocarbons (e.g., MX, OX). Since the toluene methylation unit enhances the PX content of the reformate $C_8$ fraction, the size of the PX separation section can be reduced. This is a significant advantage since the PX separation section is one of the most expensive processes in an aromatics complex both from a capital cost and from an operating expense perspective.

After recovery of PX in the PX separation section, the remaining PX-depleted stream is sent to a transalkylation unit where toluene is produced by the transalkylation of benzene with xylenes. Any liquid phase or vapor phase transalkylation unit can be used in the embodiments disclosed herein, but one preferred unit employs the multi-stage catalytic system described in U.S. Pat. No. 7,663,010, the entire contents of which are incorporated herein by reference. The transalkylation unit can be used to generate benzene and toluene using xylenes and $C_{9+}$ aromatic feeds as described in U.S. Pat. No. 8,940,950, the entire contents of which are incorporated herein by reference, of which the benzene and/or toluene can be used as feed to the toluene methylation unit to produce higher PX purity feeds to the PX recovery stages. Other transalkylation processes may be utilized herein that are similar to the transalkylation processes described in U.S. Pub. No. 2016/0220987, U.S. Pub. No. 2016/0221895, or U.S. Pub. No. 2016/0221896, the entire contents of each being incorporated herein by reference. Additionally, some of or all off site benzene, or import benzene feeds, can be transalkylated with $C_{9+}$ aromatic feeds to generate toluene and/or xylenes. Finally, the $C_{9+}$ aromatic molecules can be fractionated into a concentrated $C_9$ stream consisting of propylbenzenes and methylethylbenzenes which is transalkylated with benzene to produce toluene and EB. The toluene and EB can then be processed in the toluene methylation unit to generate PX and light olefins for recovery. In addition to the toluene produced by the reforming section and/or the transalkylation section, imported toluene can also be fed to the toluene methylation unit for incremental PX production. Such imported toluene is preferably oxygen stripped and tanks for storage of such imported toluene are preferably nitrogen blanketed.

Referring now to FIG. 1, a process and system for producing PX according to some embodiments is shown. In the process of FIG. 1 a naphtha feedstock is supplied by line 11 to a catalytic reformer (e.g., a semi-regenerative reformer, a cycle reformer or a continuous catalytic reformer, etc.) 12. The naphtha feedstock may be derived from any suitable source, such as, for example, straight-run naphtha, naphtha from distillate or vacuum gas oil (VGO), residual conversion effluent, condensate, etc. The effluent from the catalytic reformer 12 (which may be generally referred to herein as "catalytic reformate") is a complex mixture of aliphatic and aromatic hydrocarbons and, after optional removal of the $C_{5-}$ fraction in a depentanizer (not shown), the remaining $C_{6+}$ fraction is fed by line 13 to a reformate splitter 15. Hydrogen is also generated in the catalytic reformer 12 and is removed via line 14 for use in various units in a refinery, or in a cyclohexane unit or any other petrochemical process if the aromatics complex is not erected next to a refinery. Alternatively, the hydrogen in line 14 can be sold as export, or used in fuel, or flared.

The reformate splitter 15, which can optionally be a dividing-wall distillation column, separates the $C_{6+}$ fraction in line 13, in one embodiment, into a $C_{6-}$ containing overhead stream in line 16, a $C_7$ containing intermediate stream in line 31, and a $C_{8+}$ containing bottoms stream in line 51. The $C_{6-}$ containing overhead stream may also contain some or all of the toluene and/or $C_8$ aromatics present in line 13 along with their non-aromatic co-boilers, depending on specific economic objectives. In another embodiment (not shown), the reformate splitter 15 separates the $C_{6+}$ fraction in line 13 into a $C_{7-}$ containing overhead stream and a $C_{8+}$ containing bottoms stream, omitting the recovery of an intermediate stream. Again, the $C_{7-}$ containing overhead stream in this alternative embodiment may also contain some or all of the $C_8$ aromatics present in line 13 along with their non-aromatic co-boilers, depending on specific economic objectives.

Returning to FIG. 1, the $C_{6-}$ containing overhead stream, or the $C_{7-}$ containing overhead stream in the alternate embodiment, from the reformate splitter 15 is sent via line 16 to an extraction section 17, which can be a liquid-liquid extraction process, an extractive distillation type process or a hybrid thereof. Non-aromatics raffinate is removed from the extraction section 17 via line 18 and can be used in an olefins oligomerization or reformate alkylation unit, or as feed to a steam cracker or to the refinery gasoline pool, or as fuel. The raffinate in line 18 can also be used as feed to an aromatization unit to produce additional aromatic molecules while generating hydrogen. The aromatics product from extraction section 17 is removed via line 19 and is supplied to a benzene column 21, optionally after pretreatment with clay, a molecular sieve catalyst (e.g., MWW), or hydrotreatment, to remove trace olefins or other low level impurities. Entrained water is removed from the aromatics extraction product in benzene column 21 and a benzene product is collected via line 22, typically as a side stream from the benzene column 21. The benzene column bottoms product is rich in toluene, although it may also contain some trace xylenes and heavier alkylaromatics (e.g., $C_{12}$-$C_{16}$ alkylaromatics), and is sent via line 23 to a toluene methylation section or unit 32. Specifically, in some embodiments, the benzene column bottoms product may have at least 80 wt % toluene, or at least 95 wt % toluene; however, concentrations of toluene within line 23 may be lower than these values in other embodiments. The benzene in line 22 can either be recovered via line 25 or for sale or hydrogenation to produce cyclohexane, or can be fed to a transalkylation section or unit 41 for additional toluene and xylene production. Additionally, while not shown in FIG. 1, it should be appreciated that in at least some embodiments, benzene in line 22 can be either additionally or alternatively sent to methylation unit 32.

The toluene methylation unit 32 also receives the $C_7$ containing intermediate stream from the reformate splitter 15 via line 31 together with a supply of methylating agent (not shown in FIG. 1), typically methanol and/or dimethyl ether. It should be noted that the split between line 16 ($C_{6-}$ containing overhead stream from the reformate splitter 15) and line 31 ($C_7$ containing intermediate stream from the reformate splitter 15) can be used to effectively control the level of non-aromatics sent to the toluene methylation unit 32 since non-aromatics exiting reformate splitter 15 via line 16 to the extraction section 17 will be removed via line 18. Hence, additional flow through line 16 will reduce overall non-aromatics content in the feed to the toluene methylation unit 32.

Toluene methylation unit 32 may operate according to any suitable toluene alkylation with methanol process, including any fixed-bed, fluidized-bed, or moving bed process. In at least some embodiments, the toluene methylation unit 32 employs the processes similar to those described in U.S. Pat. Nos. 5,563,310 and 6,642,426, the entire contents of which are incorporated herein by reference. In the toluene methylation unit 32, toluene from lines 23 and 31, optionally together with benzene from column 21, is reacted with methanol to produce xylenes and water. In some instances, $C_8$ aromatics are also fed to the toluene methylation unit 32 via lines 23 and 31, to carry out ethylbenzene dealkylation to benzene in the toluene methylation unit 32, with possible subsequent benzene methylation to toluene or xylenes in said section 32.

The toluene may be routed through a toluene furnace and/or heat exchange equipment (not shown) prior to entering the toluene methylation unit 32 to vaporize the toluene and heat it to the temperature required to maintain the methylation reaction, which is dependent on the type of catalyst(s) used for the methylation process. Some catalysts require the toluene to be preheated to 400° C. while other catalysts require the toluene to be preheated to 600° C. The toluene can be heated to these temperatures in process heat exchanger equipment and/or furnaces, depending on the available heat sink in the process. Toluene that is heated to high temperatures, for example in a furnace, may reach temperatures that decompose the toluene to coke or heavier hydrocarbons which can impact the heat transfer rate. This decomposition rate can be reduced by co-feeding a diluent with the toluene upstream of the heat transfer equipment, such as nitrogen, hydrogen, fuel gas, steam, or a combination thereof. The molar ratio of these diluents to toluene can vary from 0.01 to greater than 10. Toluene decomposition can also be managed using the proper metallurgy for tubes, either in the convection section or radiant section, as one having ordinary skill in the art will understand. Examples include carbon steel, stainless steels, titanium, or other alloys. Special coatings and applications may also be used to minimize toluene decomposition effects and minimize coking. Additionally, additives may be used to minimize toluene coking.

The efficiency of the methylation reaction improves as the methylating agent, typically methanol, is broadly and widely distributed within the reactor. The methylating agent can be introduced into the fixed bed or fluid bed reactor in a number of different ways, such as via a single injection point, several injection points, or even via a sparger arrangement. The methylating agent can be dispersed into the reactor either through nozzles that are flush to the reactor vessel or through an internal distribution network. The number of nozzles flush to the reactor can be one, a few or many. Alternatively, the methylating agent can be introduced into the fixed bed or fluid bed through an internal distributor. The internal distributor may be a single injection point, a few injection points or many injection points. In the case of a few or many injection points, the distributor may contain arteries branching off of one or more common headers, and additional sub-arteries may branch off of each artery to form a network of arteries. The arteries may be designed to have a uniform diameter, either the same or different diameter as the common headers, or be tapered in various diameters and different lengths. Along each common header or artery there may be one or several or many nozzles to introduce the methylating agent. The size and length of these nozzles may be similar or different depending on the required distribution of the methylating agent into the reactor. The internal distributor, arteries, and nozzles may be insulated if used in a fluid bed or fixed bed reactor. The decision to insulate or not can change the metallurgical requirements, which can range from carbon steel or to stainless steels or to titanium or other types of alloys commonly used. The bulk temperature of the methylating fluid and the skin temperatures inside of the distribution network are preferred to be below the decomposition temperature of the methylating agent, which is known to one having ordinary skill in the art. The decomposition rate of the methylating agent can be reduced by co-feeding a diluent, such as nitrogen, hydrogen, fuel gas, steam, or a combination thereof. The molar ratio of these diluents to methylating agent can vary from 0.01 to greater than 10. In some embodiments, the distribution system for a methylating agent is a fractal distributor which contains an order of magnitude number of arteries and nozzles located both radially and axially throughout the reaction zone. The fractal distribution system can be designed to introduce the methylating agent at the same or different rate axially inside the reactor. The axial distribution can also be controlled having two or more fractal distributors with rates of methylating agent controlled externally from the reactor via common engineering methods, i.e., valves, pumps, restriction orifices, etc.

Referring still to FIG. 1, the process off-gas from the toluene methylation unit 32 is collected by line 33 and can be used in an olefins oligomerization unit (not shown) or a reformate alkylation unit (not shown), or can be sent to a steam cracker or refinery for olefins recovery (not shown), or used as fuel gas. Other processing operations for off-gas in line 33 may be similar to those discussed in U.S. Pub. No. 2014/0100402, the entire contents of which are incorporated herein by reference. The remainder of the product from the toluene methylation unit 32 is fed via line 34 to a xylene distillation column 35, which divides the methylation product into a PX rich $C_8$ aromatics overhead stream and a $C_{9+}$ bottoms stream. Because the quantity of the $C_9$ aromatics is small, the residence time of the $C_9$ aromatics in the distillation column bottoms circuit, i.e., reboiler circuit, can be very high. These $C_9$ aromatics can then polymerize or condense into higher hydrocarbon components when exposed to high temperature and a long period, which may foul the bottoms circuit or heat exchange equipment. Additives can be used to control the rate of heavy polymerization or condensation. Alternatively another source of $C_9$ aromatics can be added to the distillation column to dilute the $C_9$ aromatics from the toluene methylation process. This additional source of $C_9$ aromatics can be introduced either continuously or in batch mode or in semi-batch mode, and purged from the system along with the toluene methylation $C_9$ aromatics, either continuously or batch or semi-batch mode. The additional source of $C_9$ aromatics can be introduced into the distillation column at any location in the distillation column as one having ordinary skill will be able to determine.

Prior to the xylene distillation tower 35, the methylation effluent stream in line 34 from the toluene methylation unit 32 may be fed through a toluene distillation tower (not shown) to recover unconverted toluene from the xylenes and heavier components. Fresh toluene may also be fed through the toluene distillation tower. The feed point to the toluene distillation tower for the methylation effluent stream in line 34 and fresh toluene may be the same or different as one having ordinary skill in the art will be able to determine. Additionally, there may be other streams that can be fed to the toluene distillation tower, for example a xylenes and heavier stream from a naphtha reformer, xylene isomerization unit, disproportionation unit, transalkylation unit, or any other unit that may contain toluene and heavier aromatics. The toluene from the toluene distillation unit is typically recovered as a liquid overhead product, after condensing via conventional cooling methods such as an air fin, water cooler or process cooler, or combination thereof, either in parallel or series configuration. The toluene may also be recovered as a vapor product, either in the overhead of the distillation tower, upstream of any cooling equipment, or as a side stream from the distillation column. Likewise, the toluene can be recovered as a liquid product from one of the trays in the distillation tower, for example, 3-5 trays below the overhead of the distillation tower. This is particularly effective if the distillation tower contains a component or components lighter than toluene, for example, water or light hydrocarbons, which could reduce the concentration of toluene by dilution. The distillation column to separate toluene from heavier aromatics and impurities may also be a divided wall column, with one or more than one partitions. The recovered toluene may then be recycled back to the toluene methylation unit 32 and the heavier components sent downstream for further processing.

Referring still to FIG. 1, the PX rich $C_8$ aromatics overhead stream from the xylene distillation column 35 is sent via line 36 to a separation section 37, where PX product is recovered via line 38. The PX rich $C_8$ aromatics overhead stream in line 36 may have any PX concentration; however, in at least some embodiments the PX concentration is preferably greater than equilibrium concentration levels (i.e., greater than ~24 wt % based on the total weight of xylenes in line 36). In other embodiments, the PX concentration in line 36 is equal to or greater than 75 wt % based on the total weight of xylenes within line 36.

The separation section 37 can be based on an adsorption process or a crystallization process or any combination of both (or some other PX recovery process), but in any case it can be optimized to manage PX separation from three separate streams, namely one with ~20% PX content ($C_8$ portion of the reformate), one with preferably ≥75% PX content (toluene methylation process effluent), and one with equilibrium (~24%) PX content (transalkylation and/or isomerization effluent). Such optimization will result in substantial downsizing of the overall separation section 37 as well as considerable savings in utilities consumption. Such optimization may include feeding the PX enriched xylenes stream independent of equilibrium xylenes stream as described in U.S. Pat. Nos. 8,168,845; 8,529,757; 8,481,798; 8,569,564; 8,580,120; and 9,522,863, the entire contents of which are incorporated herein by reference. Alternatively, a PX enriched product or intermediate product from the adsorption process, which has a PX purity less than 99.7 wt %, can be fed to the crystallization unit to enrich the PX to higher concentrations. Likewise, the crystallization product or intermediate product having a PX purity less than 99.7 wt % may be fed to the adsorption process to enrich the PX to higher concentrations.

Invariably there will be a small amount of toluene present in the xylenes feed to the PX separation section 37. If a Simulated Moving Bed (SMB) Adsorption unit is used to recover PX, a fraction of the toluene present in the xylenes feed will be fractionated as a "crude" toluene product, which may contain trace amounts of xylenes or water. This stream can be sent directly to the toluene methylation unit 32 without any treatment to remove trace xylenes or water, since in at least some embodiments the feed to the toluene methylation unit 32 generally contains water co-feed to improve methanol utilization and to suppress feed preheat coking. A combination of both an adsorption process and a crystallization process in separation section 37 may include a small SMB unit (not shown) and a small crystallization unit (not shown) operating in series or in parallel, with the SMB unit primarily dedicated to PX separation from equilibrium xylenes streams and the crystallization unit primarily dedicated to PX separation from the PX enriched stream.

Regardless of the specific PX recovery process(es) used in separation section 37, in addition to the PX product in line 38, a PX depleted stream is also produced from separation section 37 via line 39. The PX depleted stream is then routed via line 39 to transalkylation unit 41, where additional toluene is produced through transalkylation of benzene with xylenes. In addition, in the transalkylation unit 41, $C_9$ aromatics, $C_{10}$ aromatics and some $C_{11}$ aromatics are converted to equilibrium xylenes either directly or by reaction with benzene or toluene routed from other parts of the process (e.g., benzene from benzene column 21 via lines 22, 24).

While there are many options to optimize PX production in an aromatics complex operating a toluene methylation unit (such as toluene methylation unit 32) and a transalkylation unit (such as transalkylation unit 41), since toluene methylation is highly selective to PX, and transalkylation produces a mixed xylenes product, in a preferred embodiment, all toluene introduced or produced in the aromatics complex is sent to the toluene methylation unit 32 rather than the transalkylation section 58. Toluene sources in the complex, illustrated in FIG. 1, include toluene from the reformate splitter 15 in optional line 31, toluene from the benzene column 21 in line 23, unconverted toluene in the effluent from the toluene methylation unit, "crude" toluene from the PX separation section 37, and toluene produced in the transalkylation unit 41, as well as any stream of imported toluene (not shown). Thus, little or no toluene in the effluent from the transalkylation unit 41 is recycled to the transalkylation unit 41. In this embodiment, benzene from benzene column 21 is sent to transalkylation unit 41 via lines 22, 24 in an amount that optimizes the methyl to ring ratio such that xylenes production in transalkylation unit 41 is maximized. The benzene that is not processed in transalkylation unit 41 can be recovered for sale or hydrogenation to produce cyclohexane or can be fed to the toluene methylation unit 32 for additional xylenes production. The effluent from the transalkylation unit 41, which may comprise benzene, toluene, equilibrium xylenes, EB, and $C_{9+}$ aromatics, is supplied by line 42 to a stabilizer column 43.

In stabilizer column 43, which may optionally comprise a dividing wall column, a $C_7$ containing overhead stream is removed via line 44 and a $C_{8+}$ containing bottoms stream is collected in line 45 and fed to a xylene rerun column 52 via line 47 and/or to reformate splitter 15 via line 46. In some embodiments, toluene in overhead stream 44 is recycled to transalkylation unit 41 via line 44b, recycled to methylation unit 32 via line 44a, is sold as a product, sent to a mogas blending section (not shown), and/or sent to a solvents production section (not shown). In at least some preferred embodiments, toluene in overhead stream 44 is routed to methylation unit 32 to further facilitate the production of PX from methylation unit 32. In addition, in some embodiments benzene in overhead stream 44 may be recycled to transalkylation unit 41 via line 44b, recycled to toluene methylation unit 32 via line 44a, and/or is sold as a product. In at least some preferred embodiments, benzene in overhead stream 44 is sent to transalkylation unit 41 via line 44b since benzene is utilized within translkylation unit 41 to transalkylate PX depleted $C_8$ aromatics supplied by, e.g., line 39.

Referring still to FIG. 1, in at least some embodiment, $C_{8+}$ containing bottoms stream 51 includes some amount of EB (e.g., at least 10 wt %, 20 wt %, 40 wt %, etc.). As a result, the $C_{8+}$ containing bottoms stream 51 is routed to a de-methylation unit 81 to convert at least some (or most) of the EB within stream 51 into toluene. For example, in some embodiments, at least 50 wt % of the EB within stream 51 is converted to toluene within de-methylation unit 81. In other embodiments, at least 75 wt %, at least 90 wt %, at least 95 wt %, at least 99 wt %, or more (including all) of the EB within line 51 is converted to toluene within de-methylation unit 81.

Any known de-methylation process for converting EB to toluene may be used within de-methylation unit 81. For example, in at least some embodiments, de-methylation unit 81 employs a de-methylation catalyst, such as that employed in U.S. Pat. No. 4,177,219, the entire contents of which are incorporated herein by reference. In still other embodiments, any other process suitable for converting EB to toluene may be used in place of de-methylation unit 81. In this embodiment, de-methylation unit 81 outputs an effluent stream 82, which is subsequently fractionated in de-toluenizer column 83 into a $C_{7-}$ fraction and a $C_{8+}$ fraction. The $C_{7-}$ fraction is routed to benzene column 21 via line 84, where it is then directed into toluene methylation unit 32 via line 23 as described above. In addition, the $C_{8+}$ fraction is directed to xylene rerun column 52 via line 85, so that xylenes within $C_{8+}$ fraction 85 may be routed to separation section 37 as described in more detail below.

In many xylene production units, EB is converted by EB dealkylation to less valuable benzene. Thus, the direct conversion of EB to toluene via de-methylation unit 81 produces a more valuable effluent (toluene) that can be fed to methylation unit 32 to enhance production of PX as previously described above. In addition, in complexes where EB is converted to xylenes by EB reforming processes, such conversion is thermodynamically limited to 27-30% per pass and therefore involves a high amount of recycle and energy consumption. By contrast, EB conversion to toluene (e.g., via de-methylation unit 81) is kinetically controlled and thus can be carried out at close to 100% per pass as previously described above. Finally, any xylene losses through de-methylation in an EB de-methylation unit (e.g., unit 81) are effectively mitigated by feeding the resulting toluene in line 84 to methylation unit 32, since additional xylenes (particularly PX) will be produced within methylation unit 32 as a result of the additional toluene feed. Therefore, the conversion of additional toluene from EB within catalytic reformate 13 (e.g., in de-methylation unit 81) enhances the production efficiency (in terms of PX production) for the process and system of FIG. 1.

The xylene rerun column 52 separates $C_{9+}$ aromatics from both the $C_{8+}$-containing bottoms stream 45 from stabilizer column 43 and the $C_{8+}$ fraction 85 from de-toluenizer column 83. The separated $C_{9+}$ aromatics from column 52 are then sent via line 54 to a heavy aromatics column 72, which also receives the $C_{9+}$ bottoms stream from the xylene column 35 via line 71. A $C_8$ rich overhead stream is removed as overhead from the xylene rerun column 52 via line 53 and is fed via line 56 to separation section 37 where PX product is collected via line 38. Alternatively or additionally, the $C_8$ rich overhead stream in line 53 may be sent to transalkylation unit 41 via line 55. Further, in still other embodiments, the $C_8$ rich overhead stream in line 53 may be alternatively or additionally sold as a mixed xylene product (e.g., when economic factors favor the selling of mixed xylenes over a PX-rich stream such as produced in line 38). In at least some embodiments, the $C_8$ rich overhead stream in line 53 comprises xylenes at equilibrium or near equilibrium concentrations (~24 wt % PX, ~26 wt % OX, ~50 wt % MX). Optionally, where OX production is desired, part or all of the bottoms stream from the xylene rerun column 52 can be fed via line 61 to OX column 62. OX product is collected overhead via line 63, while the OX column bottoms heavies are sent to the heavy aromatics column 72 via line 64.

In embodiments where all of $C_8$ rich overhead stream is sent to transalkylation unit 41 via lines 53, 55, and none of $C_8$ rich overhead stream is routed to separation section 37, the size of the separation section 37 may be substantially reduced. Specifically, in these embodiments, the only stream flowing to separation section 37 is the effluent from toluene methylation unit 32 in line 34. As the PX content of the effluent in line 34 is increased further above equilibrium concentration levels (e.g., >24 wt %), the separation section 37 size can be further reduced, which thereby provides greater efficiency and a reduction in operating costs for the process.

The heavy aromatics column 72 removes $C_9$ aromatics, $C_{10}$ aromatics and some $C_{11}$ aromatics from the streams 54 and 71 and feeds these components via line 73 to transalkylation unit 41, while heavier compounds in the streams 54 and 71 are collected via line 74 for supply to the fuel oil pool and/or to another hydrocarbon processing unit which may be able to upgrade the heavier compounds to a more desirable, valuable product or products. In some embodiments, the overhead stream in line 73 may be combined with benzene and/or xylene streams to produce additional toluene within transalkylation unit 41.

It should be noted that for the embodiment of FIG. 1, no xylene isomerization process is utilized. Xylenes isomerization processes typically include either vapor-phase processes, or liquid-phase processes. Examples of vapor-phase isomerization processes include EB-dealkylation type isomerization, where PX-depleted xylenes are isomerized to equilibrium xylenes and EB is converted to benzene and light gas, and EB-reforming type isomerization, where PX-depleted xylenes are isomerized to equilibrium xylenes and EB is converted to additional xylenes. In addition, for liquid phase isomerization processes PX-depleted xylenes are isomerized to equilibrium xylenes and EB remains largely (or totally) unconverted. Isomerization processes are typically at the core of the xylene loop, which typically comprises a $C_8$ aromatics fractionation column (e.g., column 35), followed by a PX separation unit (e.g., separation unit 37), followed by PX-depleted xylenes isomerization to equilibrium xylenes (e.g., via vapor-phase and/or liquid-phase isomerization), and then finally again followed by the C8 aromatics fractionation column. Xylene loop process schemes are typically used to produce a PX product stream, such as PX product stream 38 shown in FIG. 1. However for the embodiments disclosed herein, no xylene isomerization process is employed for PX depleted stream 39 to return the xylenes in line 39 back to equilibrium or near equilibrium concentrations. Rather, as described above, the PX depleted stream 39 (which may include varying concentrations of MX and OX) is fed to transalkylation unit in an effort to produce, among other things, additional toluene that is then routed back to methylation unit 32 to further increase the production of PX as described above. The use of isomerization process units, particularly vapor phase isomerization units, requires a relatively large amount of energy, so that the removal thereof from the process of FIG. 1 also allows for an increase in the energy efficiency for producing PX therewith.

Figure 2:
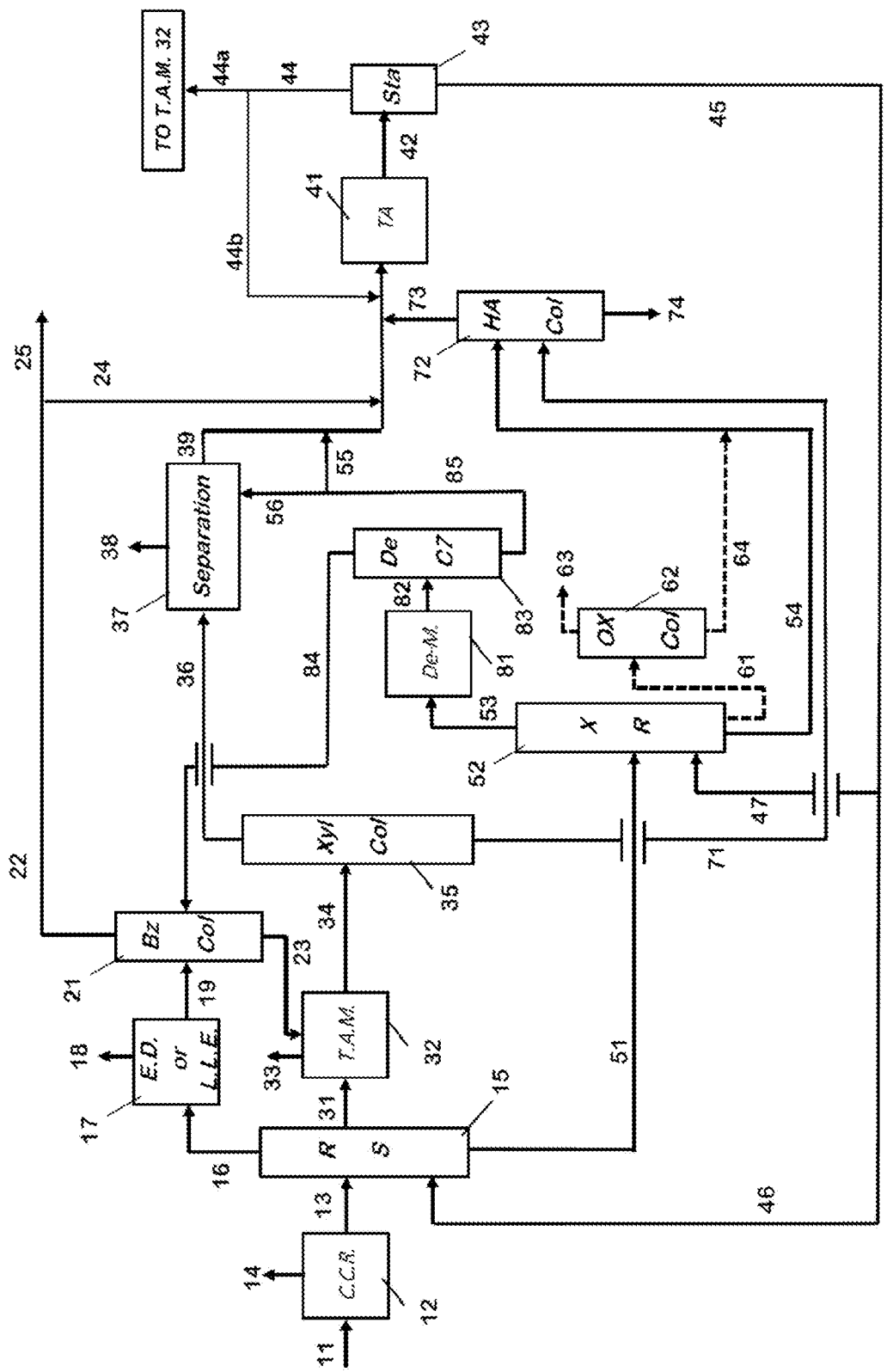
FIG. 2 is a flow diagram illustrating another process and system for producing PX from catalytic reformate according at least some embodiments disclosed herein.

Referring now to FIG. 2, another process and system for producing PX according to some embodiments is shown. The process and system of FIG. 2 are substantially similar to the process and system of FIG. 1. As a result, like numerals are used to denote like components and the discussion below will concentrate on the features of the process and system of FIG. 2 that are different from those in the process and system of FIG. 1.

In particular, in the process shown in FIG. 2, de-methylation unit 81 is disposed downstream of xylene rerun column 52 and is configured to receive $C_8$ rich overhead stream 53. As with the embodiment of FIG. 1, de-methylation unit 81 is configured to convert at least some, most, or substantially all of the EB within line 53 into toluene. As a result, de-methylation unit 81 may be configured the same as previously described above. De-methylation unit 81 outputs an effluent stream 82, which is subsequently fractionated in de-toluenizer column 83 into a $C_{7-}$ fraction and a $C_{8+}$ fraction. The $C_{7-}$ fraction is routed to benzene column 21 via line 84, while the $C_8$ rich de-toluenizer bottoms stream is fed via lines 85, 56 to separation section 37 where PX product is collected via line 38 as previously described above. Alternatively or additionally, the $C_8$ rich bottoms stream in line 85 may be sent to transalkylation unit 41 via line 55.

Figure 3:
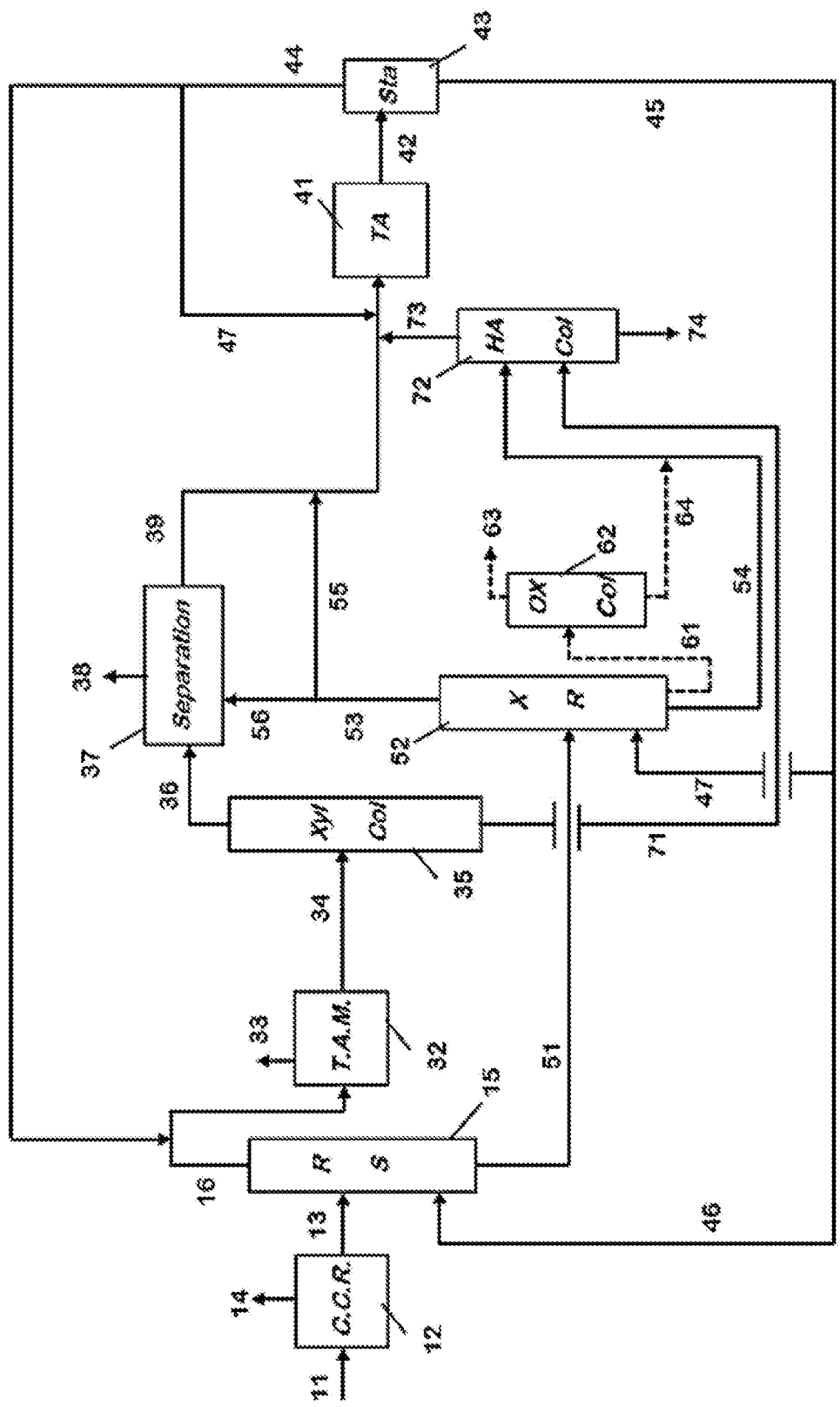
FIG. 3 is a flow diagram illustrating another process and system for producing PX from catalytic reformate according at least some embodiments disclosed herein.

Referring now to FIG. 3, another process and system for producing PX according to some embodiments is shown. The process and system of FIG. 3 are substantially similar to the process and system of FIG. 1. As a result, like numerals are used to denote like components and the discussion below will concentrate on the features of the process and system of FIG. 2 that are different from those in the process and system of FIG. 1.

In particular, in the process shown in FIG. 3, there is no provision for non-aromatics or benzene recovery and so the extraction section 17 and the benzene column 21 of FIG. 1 are omitted. Thus, in this modification, after the $C_{5-}$ fraction of the reformer effluent is removed in a depentanizer (not shown), the effluent from catalytic reformer 12 is fed via line 13 to a reformate splitter section 15 which separates a $C_6/C_7$ containing overhead stream in line 16 from a $C_{8+}$ containing bottoms stream in line 51. The $C_6/C_7$ containing overhead stream is fed via line 16 to the toluene methylation unit 32, with no benzene extraction step, and, as in the embodiment of FIG. 1, the $C_{8+}$ containing bottoms stream is fed via line 51 to the xylene rerun column 52. Another noticeable change affects the stabilizer column 43 overhead liquid $C_6/C_7$ stream which is collected via line 44. As shown in FIG. 2, the stream in line 44 can be recycled to the inlet (or upstream side) of the toluene methylation unit 32. In addition, the stream in line 44 may additionally or alternatively be recycled to transalkylation unit 41 via line 47. Factors impacting the decision to recycle a portion of stream 44 to transalkylation unit 41 versus toluene methylation unit 32 include desired, for example, catalyst cycle length in the transalkylation section (which could be extended by the presence of lighter components such as $C_6/C_7$ in the feed to the transalkylation section) and the desired methyl/ring ratio in the transalkylation unit 41.

In addition, while not specifically shown, it should be appreciated that de-methylation unit 81 may be employed in the embodiment of FIG. 3 in either or both of the configurations shown in FIG. 1 and FIG. 2. Thus, in this embodiment, it is fully contemplated that additional toluene may still be converted from EB within the catalytic reformate stream 13, so that PX production efficiency may be further enhanced for the embodiment of FIG. 3 as previously described above. Particular reference will now be made to the following non-limiting example.

EXAMPLE 1

This simulated example illustrates how the addition of a toluene alkylation with methanol unit increases the PX output of an aromatics complex based on the same feedstock as a conventional aromatics complex where xylenes are generated in the reforming and transalkylation sections. In this example, it is assumed that all xylenes will be converted to PX (i.e., no OX production). The results are shown in Table 1 below.

TABLE 1

| BPD 29000 Kta 1245.3 | | | | | | | |
|---|---|---|---|---|---|---|---|
| | | Xylenes Recovery (only) | | Xylenes Recovery and Transalkylation | | Xylenes Recovery with TAM and Transalkylation | |
| | CCR Reformate | Percent | KTA | Percent | KTA | Percent | KTA |
| H2 | 4.0 | 49.8 | 3.7 | 46.4 | 3.0 | 37.6 | 3.3 | 41.3 |
| C1 | 1.3 | 16.2 | 0.0 | 0.0 | 0.0 | 0.0 | 0.0 | 0.0 |
| C2 | 2.1 | 26.2 | 0.0 | 0.0 | 0.0 | 0.0 | 0.0 | 0.0 |
| Fuel | | 0.0 | 5.0 | 62.5 | 10.0 | 127.9 | 10.5 | 130.8 |
| C3 | 2.8 | 34.9 | 0.0 | 0.0 | 0.0 | 0.0 | 0.0 | 0.0 |
| C4 | 3.5 | 43.6 | 0.0 | 0.0 | 0.0 | 0.0 | 0.0 | 0.0 |
| LPG | | 0.0 | 6.3 | 78.5 | 6.3 | 78.5 | 6.3 | 78.5 |
| C5 | 2.9 | 36.1 | 0.0 | 0.0 | 0.0 | 0.0 | 0.0 | 0.0 |
| C6 | 4.4 | 54.8 | 0.0 | 0.0 | 0.0 | 0.0 | 0.0 | 0.0 |
| C7 | 3.5 | 43.6 | 0.0 | 0.0 | 0.0 | 0.0 | 0.0 | 0.0 |
| C8 | 0.9 | 11.2 | 0.0 | 0.0 | 0.0 | 0.0 | 0.0 | 0.0 |
| Raffinate | | 0.0 | 11.7 | 145.7 | 11.7 | 145.7 | 11.7 | 145.7 |
| $B_z$ | 3.5 | 43.6 | 6.7 | 83.6 | 15.7 | 195.7 | 10.9 | 135.2 |
| Tol | 18.0 | 224.2 | 0.0 | 0.0 | 0.0 | 0.0 | 0.0 | 0.0 |
| Xyl | 24.0 | 298.9 | 0.0 | 0.0 | 0.0 | 0.0 | 0.0 | 0.0 |
| EB | 4.8 | 59.8 | 0.0 | 0.0 | 0.0 | 0.0 | 0.0 | 0.0 |
| Px | | 0.0 | 23.0 | 286.9 | 45.0 | 560.9 | 53.1 | 661.8 |
| $A_9$ | 18.0 | 224.2 | 0.0 | 0.0 | 0.0 | 0.0 | 0.0 | 0.0 |
| $A_{9/10+}$ | 4.9 | 61.0 | 0.0 | 0.0 | 0.0 | 0.0 | 0.0 | 0.0 |
| $A_{11+}$ (FO) | 1.4 | 17.4 | 1.4 | 17.4 | 1.4 | 17.4 | 2.2 | 27.4 |
| Mogas | | 0.0 | 42.1 | 524.3 | 6.8 | 84.9 | 6.1 | 76.0 |
| MeOH (HC) | 0 | 0.0 | 0.0 | 0.0 | 0.0 | 0.0 | −4.1 | −50.6 |

In Table 1, each aromatics complex employs the same feedstock (1245.3 kTa naphthas) qualitatively and quantitatively. Furthermore the reforming section provides the same product slate in all cases, the product slate being listed in column #1 entitled "CCR Reformate". Column #2 entitled "Xylenes Recovery (only)" shows PX production if only reformer xylenes are recovered (no transalkylation unit). Column #3 entitled "Xylenes Recovery and Transalkylation" shows PX production in a conventional aromatics complex, where a transalkylation unit has been added to produce additional xylenes. Column #4 entitled "Xylenes Recovery with TAM and Transalkylation" shows PX production from an aromatics complex where a toluene alkylation with methanol unit has been added to a conventional aromatics complex with a transalkylation unit.

As can be seen from Table 1, on the same feedstock and reforming section output basis, PX production for a conventional aromatics complex is 560.9 kTa while PX production for a conventional complex where toluene alkylation with methanol unit has been added is 661.8 kTa.

Furthermore, PX production is often favored over benzene production due to higher margins. Benzene conversion by transalkylation with equilibrium xylenes to make toluene, followed by the toluene methylation (e.g., recycle of toluene in line 44 to methylation unit 32 in FIG. 1) and/or the direct methylation of benzene in a methylation unit (e.g., methylation unit 32 in FIG. 1 and FIG. 2) may increase the amount of the complete PX production to ~845.5 kTa.

As described herein, by flowing a PX depleted stream from a PX separation unit (e.g., separation section 37) to a transalkylation unit (e.g., transalkylation unit 41), the need for a xylenes isomerization unit (e.g., liquid phase isomerization unit, vapor phase isomerization unit, etc.) is eliminated, since PX-depleted xylenes will be converted to toluene by transalkylation reaction with benzene in transalkylation unit 41. In addition, as also described herein, additional EB carried with the catalytic reformate (e.g., stream 13) feeding a toluene methylation process (e.g., unit 32), may be converted to toluene so that additional xylenes (particularly PX) may be further produced from the methylation unit. As a result, the expenses for constructing and operating a PX production complex (e.g., the complexes shown in FIG. 1 and FIG. 2), may be reduced, thereby improving the economic margins for PX production.

While embodiments described herein have incorporated a de-methylation unit 81 for, among other things, converting EB into toluene, it should be appreciated that in other embodiments, de-methylation unit 81 may be utilized additionally or alternatively to convert heavier aromatics, e.g., $C_{9+}$ aromatics, to more valuable xylene and/or trimethyl benzene. For example, in the embodiment of FIG. 1, at least some of the C9+ aromatics in line 51 may undergo such a conversion. Conversion of these heavier aromatics (e.g., to xylene and/or trimethyl benzene) improves the operation of transalkylation unit 41, because $C_{9+}$ aromatics stream 73 contains less ethyl- or propyl- or butyl-substituted aromatics, which can extend the operating cycle of the catalyst in transalkylation unit 41 and/or reduce the catalyst inventory requirement in transalkylation unit 41.

While various embodiments have been disclosed herein, modifications thereof can be made without departing from the scope or teachings herein. In particular, many variations and modifications of the systems, apparatus, and processes described herein are possible and are within the scope of the disclosed subject matter. Accordingly, embodiments disclosed herein are exemplary only and are not limiting. As a result, the scope of protection is not limited to the embodiments described herein, but is only limited by the claims that follow, the scope of which shall include all equivalents of the subject matter of the claims. Unless expressly stated otherwise, the steps in a method claim may be performed in any order. The use of identifiers such as (a), (b), (c) before steps in a method claim is not intended to and does not specify a particular order to the steps. Rather the use of such identifiers are used to simplify subsequent reference to such steps. Finally, the use of the term "including" in both the description and the claims is used in an open ended fashion, and should be interpreted as meaning "including, but not limited to".

The invention claimed is:

1. A process for producing para-xylene (PX), the process comprising:
   (a) separating a feed stream comprising $C_{6+}$ aromatic hydrocarbons into at least a toluene containing stream and a $C_{8+}$ hydrocarbon containing stream;
   (b) contacting at least part of the toluene containing stream with a methylating agent in a methylation unit under conditions effective to convert toluene to xylenes and produce a methylated effluent stream;
   (c) recovering PX from the methylated effluent stream in (b) to produce a PX depleted stream;
   (d) transalkylating the PX depleted stream to produce a transalkylation effluent stream, wherein the transalkylation effluent stream includes a higher concentration of toluene than the PX depleted stream;
   (e) converting at least 50 wt % of the ethylbenzene (EB) within the $C_{8+}$ hydrocarbon containing stream into toluene; and
   (f) flowing the toluene converted in (e) to the contacting in (b).

2. The process of claim 1, further comprising:
   (g) separating from the transalkylation effluent stream a $C_7$ containing stream and a $C_{8+}$ hydrocarbon containing bottoms stream; and
   (h) recycling the $C_7$ containing stream to at least one of the contacting in (b) or the transalkylation in (d).

3. The process of claim 2, further comprising recycling the $C_{8+}$ hydrocarbon containing bottoms stream from (g) to the separating in (a).

4. The process of claim 2, further comprising:
   (i) separating a $C_8$ hydrocarbon containing stream and a $C_{9+}$ aromatic hydrocarbon-containing stream from the $C_{8+}$ hydrocarbon containing stream in (a);
   (j) recycling the $C_{8+}$ hydrocarbon containing bottoms stream from (g) to the separating in (i).

5. The process of claim 4, further comprising flowing the $C_8$ hydrocarbon containing stream from (i) to at least one of the recovering in (c) or the transalkylating in (d).

6. The process of claim 4, further comprising:
   (k) separating a $C_9$ and $C_{10}$ aromatic hydrocarbon containing stream from the $C_{9+}$ aromatic hydrocarbon containing stream from (i);
   (l) flowing the $C_9$ and $C_{10}$ aromatic hydrocarbon containing stream from (k) to the transalkylating in (d).

7. The process of claim 6, further comprising:
   (m) separating a $C_{9+}$ hydrocarbon containing bottoms stream from the methylated effluent stream after (b) and before (c);
   (n) flowing the $C_{9+}$ hydrocarbon-containing bottoms stream from (m) to the separating in (k).

8. The process of claim 1, wherein the PX depleted stream comprises ortho-xylene (OX) and meta-xylene (MX) and wherein the PX depleted stream is not flowed through an isomerization reactor.

9. The process of claim 1, further comprising providing a naphtha feedstock to a catalytic reformer to produce the feed stream before the separating in (a).

10. The process of claim 1, wherein the separating in (a) further comprises separating a $C_{6-}$ hydrocarbon containing stream from the feed stream.

11. The process of claim 10, further comprising:
    (o) flowing the toluene containing stream from (a) to the contacting in (c) directly after the separating in (a).

12. The process of claim 11, further comprising:
    (p) extracting non-aromatics from the $C_{6-}$ hydrocarbon containing stream to produce a toluene containing aromatic stream;
    (q) separating a benzene stream and a toluene stream from the toluene containing aromatic stream; and
    (r) supplying the toluene stream to the contacting in (b).

13. The process of claim 12, further comprising flowing the benzene stream from (q) to the transalkylating in (d).

14. A system for producing para-xylene (PX), the system comprising:
- a catalytic reformer configured to produce a reformate stream comprising $C_{6+}$ aromatic hydrocarbons from a naphtha feedstock;
- a first separation system downstream of the catalytic reformer, wherein the first separation system is configured to separate the reformate stream into at least a toluene containing stream and a $C_{8+}$ hydrocarbon containing stream;
- a de-methylation unit configured to receive the $C_{8+}$ hydrocarbon containing stream and convert at least 50 wt % of the ethylbenzene (EB) within the $C_{8+}$ hydrocarbon containing stream into toluene;
- a toluene methylation unit downstream of the first separation system and the de-methylation unit, wherein the toluene methylation unit is configured to receive the toluene containing stream and toluene converted from EB in the de-methylation unit, and to react toluene with a methylating agent to produce xylenes that are emitted from the toluene methylation unit as a methylated effluent stream;
- a second separation system downstream of the toluene methylation unit, wherein the second separation system is configured to recover PX from the methylated effluent stream and produce a PX depleted stream; and
- a transalkylation unit downstream of the second separation system, wherein the transalkylation unit is configured to transalkylate the PX depleted stream and produce a transalkylation effluent stream that has a higher concentration of toluene than the PX depleted stream.

15. The system of claim 14, further comprising a third separation system downstream of the transalkylation unit, wherein the third separation system is configured to separate the transalkylation effluent stream into a $C_7$ hydrocarbon containing stream and a $C_{8+}$ hydrocarbon containing bottoms stream;
- wherein the $C_7$ hydrocarbon containing stream is in direct fluid communication with an upstream side of at least one of the toluene methylation unit or an upstream side of the transalkylation unit.

16. The system of claim 15, further comprising a fourth separation system configured to receive the $C_{8+}$ hydrocarbon containing stream from the first separation system, wherein the fourth separation system is configured to separate a $C_8$ hydrocarbon containing stream and a $C_{9+}$ aromatic hydrocarbon containing stream from the $C_{8+}$ hydrocarbon-containing stream.

17. The system of claim 16, wherein the $C_8$ hydrocarbon containing stream is in direct fluid communication with the second separation system.

18. The system of claim 17, wherein the $C_{8+}$ hydrocarbon containing bottoms stream from the third separation system is in direct fluid communication with an upstream side of at least one of the first separation system or an upstream side of the fourth separation system.

19. The system of claim 14, further comprising an extraction section in direct fluid communication with the toluene containing stream, wherein the extraction section is configured to remove non-aromatics from the toluene containing stream and produce a toluene containing aromatic stream.

20. The system of claim 19, further comprising a fifth separation system downstream of the extraction section, wherein the fifth separation system is configured to separate a toluene stream and a benzene stream from the toluene containing aromatic stream;
- wherein the toluene stream is in direct fluid communication with the upstream side of the toluene methylation unit; and
- wherein the benzene stream is in direct fluid communication with the upstream side of the transalkylation unit.

\* \* \* \* \*